United States Patent [19]

Shu

[11] 4,157,571
[45] Jun. 5, 1979

[54] FRAME-BY-FRAME MEMORY DISPLAY SYSTEM

[75] Inventor: Stephen K. Shu, Fountain Valley, Calif.

[73] Assignee: Del Mar Avionics, Irvine, Calif.

[21] Appl. No.: 798,765

[22] Filed: May 20, 1977

[51] Int. Cl.² .............................................. G11B 5/00
[52] U.S. Cl. .......................................... 360/8; 360/6; 360/74.1
[58] Field of Search .................... 360/8, 13, 72, 74, 5, 360/6

[56] References Cited

U.S. PATENT DOCUMENTS

| | | | |
|---|---|---|---|
| 2,904,777 | 9/1959 | Cox et al. | 360/74 |
| 3,136,465 | 6/1964 | Comstock | 360/74 |
| 3,248,030 | 4/1966 | Ganzhorn | 360/74 |
| 3,641,504 | 2/1972 | Sidline | 360/74 |
| 3,650,263 | 3/1972 | Kowalaski et al. | 360/74 |
| 3,727,203 | 4/1973 | Grossman | 360/72 |
| 3,732,380 | 5/1973 | Kimball | 360/74 |
| 3,997,913 | 12/1976 | Rittenbach | 360/8 |
| 4,006,737 | 2/1977 | Cherry | 360/74 |
| 4,056,849 | 11/1977 | Bevis | 360/74 |

OTHER PUBLICATIONS

"A Miniature 4—Channel Cassette Recorder for Physiological and Other Variables"—McKinnon, May 1974.

Primary Examiner—Vincent P. Canney
Attorney, Agent, or Firm—Smyth, Pavitt, Siegemund, Jones & Martella

[57] ABSTRACT

Apparatus under control of an operator for selectively displaying signals stored on a magnetic tape. The tape is normally first played back at a high speed, with the reproduced signal displayed at high speed to permit the operator to determine which parts of the tape to view at real-time speed. In the real-time viewing mode, a segment of the tape is played again at high speed to provide a better quality signal; the signal from the segment is converted to digital form and stored in a memory for use in creating a real-time display. The operator then can view the display of the stored signal in a variety of ways: stationary, advancing at real-time speed, or in reverse at real-time speed. The length of the segment stored is relatively short to minimize the size of the memory. After a segment is played back, the tape is brought to a stop and then moved in the opposite direction to position it for playing back the next segment.

24 Claims, 4 Drawing Figures

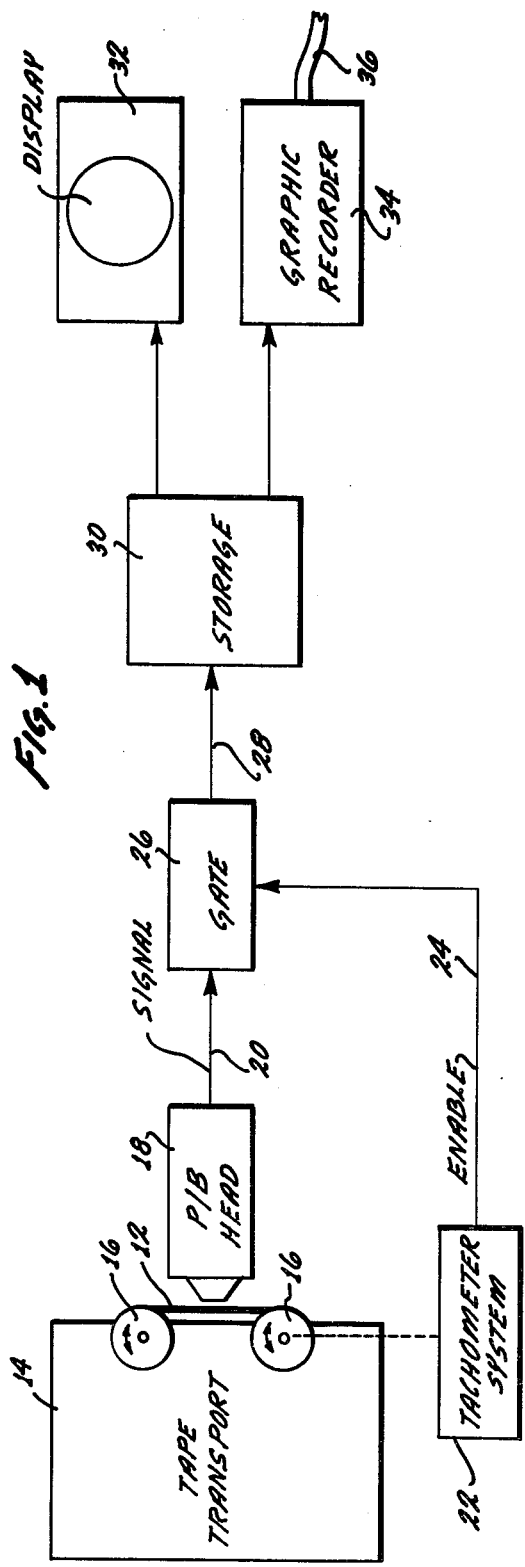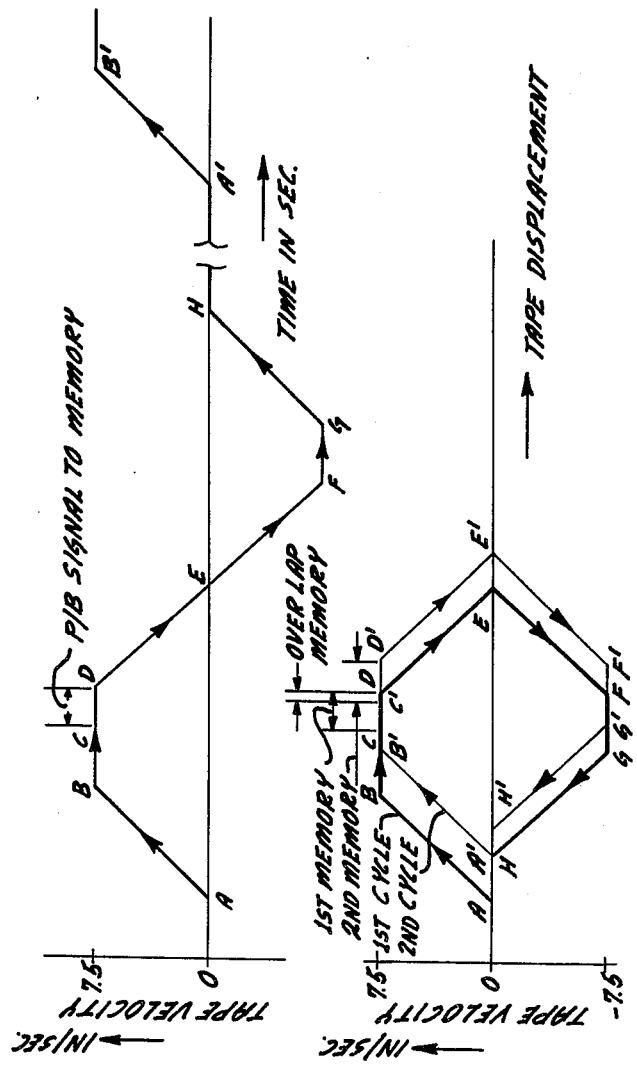

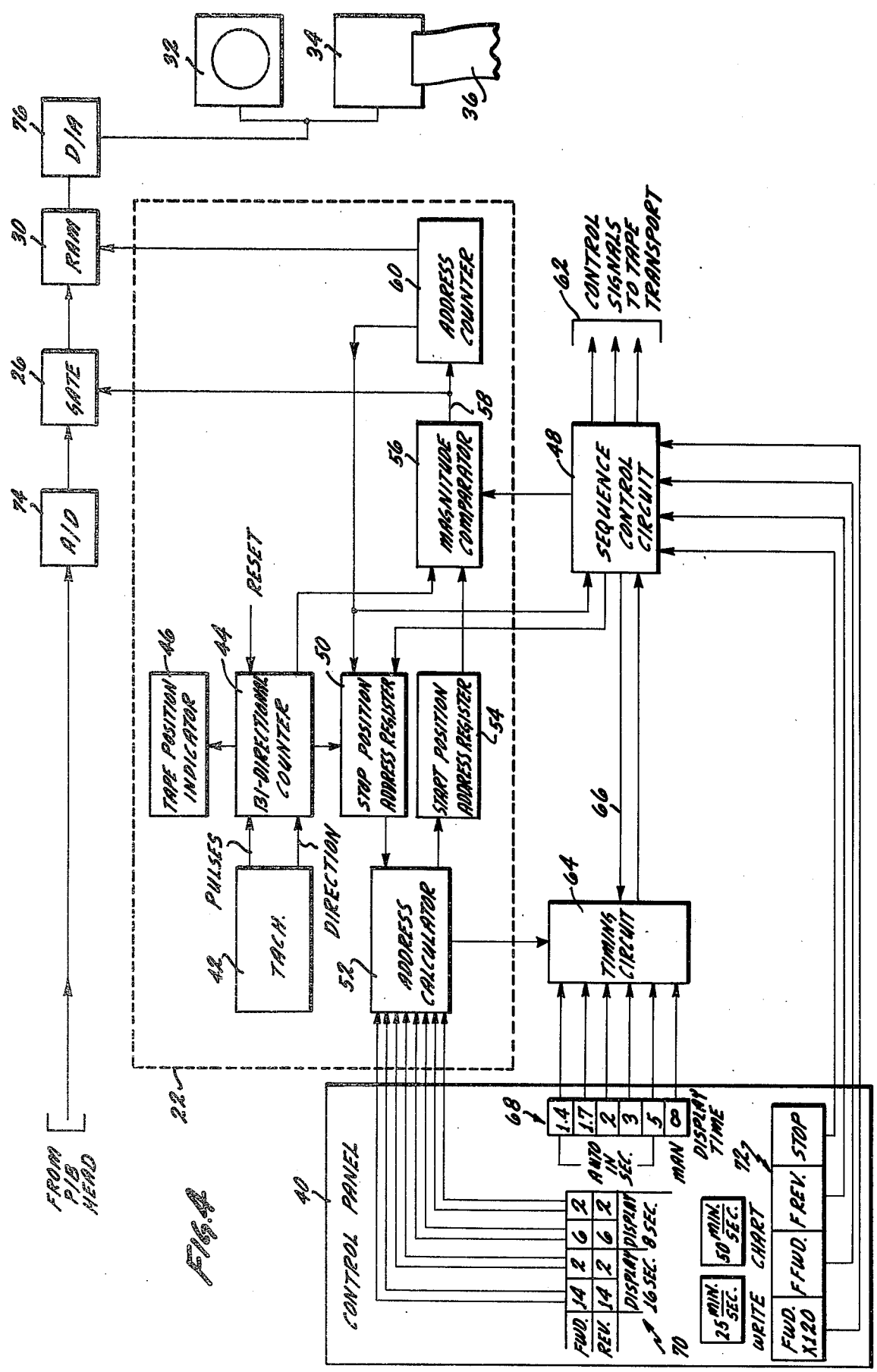

FRAME-BY-FRAME MEMORY DISPLAY SYSTEM

BACKGROUND OF THE INVENTION

1. Field of the Invention

The present invention is in the field of magnetic tape playback systems and, in particular, relates to a system in which a real-time display can be produced from a high-speed playback of a segment of a magnetic tape.

2. Description of the Prior Art

Considerable progress has been made in the last decade in recording and analyzing electrocardial signal obtained from a patient. In the Holter technique, the patient is provided with a small portable tape recorder on which his electrocardial signals are recorded over an extended period of time as the patient goes about his daily activities. It is now possible to record such signals continuously over intervals up to 24 hours on a single tape. This is accomplished by recording the tape at speeds as low as 1/16 inch per second. A recorder for this purpose is described in the copending application "Recorder for Cardiac Signals", Ser. No. 773,618, filed Mar. 2, 1977, and assigned to the assignee of the present invention.

It would be prohibitively expensive to examine an entire 24-hour recording at real-time speeds. Such tapes are normally scanned at a higher speed on specialized scanners, such as that described in U.S. Pat. No. 4,006,737 for Electrocardiographic Computer, issued Feb. 8, 1977 to Cherry and assigned to the assignee of the present invention. It is known to provide the playback scanner with the capability of displaying the signal at various speeds, but such scanners lack the ability to "freeze" the displayed action for extended study.

The electrocardial signals have significant frequency components in the lower audio range, and the design of playback heads capable of satisfactory operation at both high-speed and real-time playback speeds is difficult.

Thus, it became clear that a need existed for a playback and display system which would permit a segment of the magnetic tape to be "frozen" on the display and to be advanced and reversed at various speeds. From the standpoint of playback head efficiency, it also is desirable that the playback tape speed be a constant speed considerably higher than the real-time speed at which the tape was recorded.

SUMMARY OF THE INVENTION

The frame-by-frame memory display system of the present invention fills the above-described need by providing apparatus in which the magnetic tape, in the frame-by-frame mode, is played back at a speed significantly higher than that at which it was recorded, and in which a representation of the signal recorded on a segment of the tape can be "frozen" on the display for extended study. The representation on the display can be moved forward and backward in time at selected speeds, including real-time speed.

In the present invention this result is accomplished by the use of a storage device in which the signal reproduced at high speed is stored pending display. A relatively short segment of the magnetic tape is reproduced at high speed and stored in the memory. Thus, only a relatively small amount of storage capacity is needed. In a preferred embodiment of the invention, the storage device is a digital memory, and the reproduced signal must be converted from its analog form to a digital form suitable for storage. Depending on the type of display used, it may also be necessary to convert the data retrieved from the digital memory to an analog form compatible with the display. In a preferred embodiment of the invention, the display is a cathode ray tube, and graphic art equipment is provided for producing a relatively more permanent representation of the signal retrieved from the storage device.

In the frame-by-frame display mode, the magnetic tape is always played back in the same direction at a speed significantly higher than that at which it was recorded. The tape travels a short distance in accelerating to the playback speed, and after the selected segment has been played back, the tape continues to travel a short distance while it is being brought to a stop. If the tape were restarted to play back the next segment, a gap would exist between the successive segments. To prevent this from happening, in a preferred embodiment of the invention the tape is moved first in the forward direction for playing back a selected segment, and then the tape is moved in the reverse direction to position it properly for playing back the next selected segment. For each segment of the tape played back, the tape executes a tape movement cycle consisting of a forward motion during which playback occurs, followed by a movement in the opposite (reverse) direction.

In a preferred embodiment of the invention, the segments are selected to overlap slightly at their ends. This facilitates superposition of successive segments of the signal on the display. In other embodiments, the segments can be chosen to adjoin one another without overlapping, or a space can be provided between successive segments if desired.

In the preferred embodiment of the present invention, the segments can be chosen to form a sequence extending in the forward direction of the tape, or they may be chosen to form a sequence extending in the reverse direction on the tape. Thus, the display can be made to show the action in forward or reverse motion. The choice is implemented through selection of the distance the tape travels in the reverse direction in each tape movement cycle. For example, if the tape were moved forward three inches, then in reverse one inch, the successive segments would progress in the forward direction. On the other hand, if the tape were to advance three inches in the forward direction and then move in the reverse direction five inches, the successive segments would regress in the reverse direction.

In the preferred embodiment of the invention, a segment that has been played back and stored can be displayed as many times as desired simply by recycling it.

In a preferred embodiment of the invention, a scanning mode is provided in addition to the frame-by-frame mode to permit an expeditious previewing of the tape to determine which portions of it are of interest. In the scanning mode, the storage device is bypassed and the tape is moved continuously while the reproduced signal is displayed continuously.

After the portion of the tape which is of interest has been determined in the scan mode, the frame-by-frame mode is used by the operator to view selected segments at a real-time rate, and these segments can be incremented either forward or backward at the operator's choice. Thus, the operator has unlimited access to the signals on the tape, and a graphical presentation of any segment viewed can be obtained at will.

Because the tape is always played back at the same speed, significantly higher than that at which it is recorded, high quality signals are obtained without resorting to cumbersome and difficult-to-shield playback heads that would be required if the tape were played back at real-time speed.

It should be appreciated that the present invention accomplishes the above results with the use of a minimal amount of storage capacity. The amount of storage capacity required is determined by the duration of the segment played back during a tape movement cycle.

The novel features, which are to be characteristic of the invention, both as to organization and method of operation, together with further objects and advantages thereof, will be better understood from the following description considered in connection with the accompanying drawings.

BRIEF DESCRIPTION OF THE DRAWINGS

FIG. 1 is a block diagram of a simplified embodiment of the present invention;

FIG. 2 is a timing diagram showing the velocity of the magnetic tape during one tape movement cycle in a preferred embodiment of the present invention;

FIG. 3 is a diagram showing the relation between tape velocity and tape displacement in a preferred embodiment of the present invention; and, FIG. 4 is a block diagram of the preferred invention of the frame-by-frame memory display system of the present invention.

DESCRIPTION OF THE PREFERRED EMBODIMENT

Turning now to the drawings in which like parts are indicated by the same reference numeral, there is shown in FIG. 1 a block diagram of a simplified embodiment of the present invention. The simplified embodiment of FIG. 1 will be used to illustrate the operation of the system in terms of its major components without regard for the specific manner in which they are implemented, the latter to be described in connection with FIG. 4.

Electrocardial signals have been previously recorded on the magnetic tape 12. Most of the useful information lies in the frequency range 0–100 hz. Although two channels of electrocardial signals are recorded simultaneously in separate parallel tracks on the magnetic tape in a preferred embodiment, in the simplified embodiment of FIG. 1, only one track will be described. The magnetic tape 12 is inserted into the tape transport 14 for playback. The tape transport 14 includes the reels 16 and a drive system for turning them under control of an operator selectively in the forward and reverse directions. The playback (P/B) head 18 converts the signal stored on the magnetic tape 12 to an electrical signal on the conductor 20.

In the present invention, it is necessary to determine which point on the magnetic tape 12 is producing the signal on conductor 20 at any particular time, so that the system can locate the same point at a later stage of the cycle of operation. To accomplish this, a tachometer system 22 is associated with the tape transport 14 to generate an indexing system for the magnetic tape 12.

In the preferred embodiment, the tachometer includes an optical pickoff which generates electrical pulses as the tape 12 moves over a capstan (not shown). These successive electrical pulses are then counted to provide an accumulated total count which can be used as an index of position along the magnetic tape 12.

To display the portion of the magnetic tape 12 following a predetermined point on it, the index number corresponding to the predetermined point is compared to the continually-increasing index number generated by the tachometer system as the tape 12 moves, and when the two numbers are equal, the predetermined point has been reached. At that time, the tachometer system 22 generates an enabling signal on the conductor 24, which enables the gate 26 to pass the played back signal on the conductor 20.

The gated signal is then applied through the conductor 28 to the storage device 30 for later display. The storage device 30 is capable of accepting the serial signal on the conductor 28. In the preferred embodiment, the signal on the conductor 28 is in analog form and the storage includes a digital memory, and an analog-to-digital (A/D) converter for converting the analog input to digital form. In other embodiments, the storage device 30 may store the information in analog form. In still other embodiments, the signal on the conductor 28 may already be in digital form and the A/D converter is not required.

After an appropriate time interval, the signal stored in the storage device 30 is displayed on the display unit 32 which is a volatile display such as a cathode ray tube (CRT). Additionally, the signal stored in the storage device 30 is applied to the graphic recorder 34 to produce a permanent record 36 in chart or printed form.

The electrocardiac signals recorded on the magnetic tape 12 lie mainly in the 0–100 hz frequency range. To reproduce these signals with high fidelity at real-time rates would necessitate the use of large, well-shielded playback heads as well as amplifiers and other circuitry having a relatively flat response at frequencies approaching d.c. Such magnetic playback heads and the general nature of the problem are discussed in U.S. Pat. No. 4,006,737 to Cherry, issued Feb. 8, 1977. On the other hand, if the magnetic tape 12 could be played back at a higher speed, the playback head and circuitry could more nearly resemble that used in conventional audio playback equipment such as that used for music, thereby greatly simplifying the design of the system. However, if the tape were played back at, say, 100 times the real-time rate, the traces on the display unit 32 would fluctuate too rapidly for careful analysis, and the signal applied to the graphic recorder 34 might fluctuate too rapidly for satisfactory recording. Thus, although it appears desirable to play the tape back at a higher speed, the problems of viewing and recording the high speed signal dictate that the display 32 and graphic recorder 34 must be operated at real-time speeds. A significant advantage of the present system is that it permits the magnetic tape 12 to be played back at high speed and at the same time permits the display 32 and recorder 34 to operate at low speed (real-time).

Although in the present invention the representation produced on the display 32 and the record produced by the recorder 34 are continuous in time, the playing back of the magnetic tape 12 is intermittent. A selected segment of the magnetic tape 12 is played at high speed and the signal produced is stored in the storage device 30. Because the segment of tape is played at a speed greater than real-time, the information is stored in the storage device 30 before it is needed by the display 32 to produce a real-time display. Therefore, some of the information remains in storage until the time when it would have occurred at real-time.

Because the magnetic tape 12 is played back intermittently at high speeds, consideration must be given to the time and distance required for the tape to accelerate to and decelerate from the high speed at which it is played back. Thus, the inertia of the tape drive system must be taken into account. Accordingly, in each tape movement cycle, the tape must begin its acceleration at a time and distance well in advance of the segment of the tape chosen for playback. This is illustrated in FIGS. 2 and 3, which describe the motion of the magnetic tape during a complete tape movement cycle. Normally, the length of the segment of the magnetic tape is an integer multiple of the duration of the signal representation displayed on the display unit 32. That is, the segment equals one or more frames of the display.

In FIG. 2 the velocity of the tape in inches per second is shown as a function of time for the preferred embodiment of the present invention. If the interval CD of the graph of FIG. 2 represents the time during which the selected segment is played back, then the interval AB represents the time (0.1875 seconds) during which the tape is accelerated at 40 inches per second squared. In the preferred embodiment of the present invention the playing back is always done at 7.5 inches per second tape velocity and always in the forward direction of motion of the tape. After the selected segment has been played back, the magnetic tape is decelerated during the interval DE, reaching zero velocity instantaneously at the time E. The deceleration continues during the interval EF resulting in a negative velocity, i.e., the tape moving in a reverse direction. During the interval FG, the tape is moved in reverse at a speed of 7.5 inches per second, and this movement is maintained for approximately 0.35 seconds. Finally, the tape accelerates during the interval GH to a stop at the time H. The tape then remains at rest until the next tape movement cycle begins at the time A'.

In contrast to FIG. 2 which shows the tape velocity versus time, the graph of FIG. 3 shows the relation between the tape displacement and the tape velocity in the preferred embodiment of the present invention. FIG. 3 relates to the same tape movement cycle as FIG. 2, but describes it in a different manner. In FIG. 3, the acceleration phase is represented by the segment AB. After the tape has reached a velocity of 7.5 inches per second, it continues to move at that speed during the interval BD, during which the segment CD is played back. The tape continues to move through the interval DE as it decelerates to a stop. Thereafter, the tape is moved in the reverse direction as indicated by the points E, F, G, and H. The point H coincides with the point A' which is the starting position for the next tape movement cycle. In the next tape movement cycle, the segment C'D' is played back.

FIG. 3 shows a second tape movement cycle denoted by the letters A'-H'. The segment C'D' is seen to be displaced along the tape a short distance with respect to the segment CD of the first tape movement cycle. Also, there is an overlap C'D between the played back segments CD and C'D'.

In connection with the description of FIG. 2, the duration of time in which the tape was moved through the interval BD was not specified. That interval is determined by the operator of the apparatus and depends on whether the operator chooses to view successive segments progressing in the forward or in the reverse direction along the tape. The operator expresses his choice through a control panel (shown in FIG. 4) through which he determines the length of the segment BD by actuating certain switches located on the control panel. If it is desired to view successive segments progressing in the forward direction along the magnetic tape, the segment BD is chosen to exceed the length of the segment FG, which is the case illustrated in FIG. 3. On the other hand, if it is desired to view the successive segments as progressing in the reverse direction along the tape, the distance BD is selected to be less than the distance FG. The overlap between the successive played back segments is useful when representations of the signals played back are to be superimposed on the display. By the use of overlap, the successive representations can be accurately aligned on the face of the display.

Turning now to the block diagram of the preferred embodiment as shown in FIG. 4, it can be seen that the tachometer system 22 of FIG. 1 includes a number of sub-systems which implement the movement of the magnetic tape as described in connection with FIGS. 2 and 3. Also, the control panel 40 will be seen to permit the operator to have considerable control over the parameters of the playback and display system. The tachometer 42, in a preferred embodiment, is an optical pickoff attached to a capstan (not shown) used for driving the tape. Unlike the reels 16 of FIG. 1, the capstan has a constant diameter and, hence, each pulse produced by the tachometer 42 represents the same distance along the tape and accordingly the same time interval, namely 1/30th of a second of real recording time. The tachometer 42 also senses the direction of movement of the tape. Pulses from the tachometer 42 are applied to the bi-directional counter 44, which accumulates them. The total number of pulses accumulated is a measure of the amount of tape which has passed over the capstan, and thus can be used as an index to the tape. The count on the counter is applied to the tape position indicator 46 to give a visual indication to the operator of which portion of the tape is being played. Upon issuance of a stop command by the operator through the control panel 40, the sequence control circuit 48 generates a series of commands to cycle the tape from the position D of FIG. 2 to the end of the tape movement cycle at point H, and the tape position indicated by the bi-directional counter 44 is stored in the stop position address register 50. When a command to advance to the next segment is generated by the operator through the control panel 40, the address calculator 52 reads the tape position stored in the stop position register 50, decrements it, and stores the result in the start position address register 54. The tape transport is then commanded to accelerate in the forward direction. After the magnetic tape has reached a speed of 7.5 inches per second and when the approximate tape position is reached to reload the memory 30, the sequence control circuit 48 activates the magnitude comparator 56 which continually compares the tape position as indicated by the bi-directional counter 44 with the desired starting address which is stored in the start position address register 54. When the magnitude comparator 56 senses that the addresses are matched, it generates a signal on the conductor 58 which is applied to the gate 26 to permit the played back signals to be gated into the memory 30. When the address counter 60 has sensed that the memory has been completely reloaded, it causes the sequence control circuit 48 to generate a series of control signals on the conductors 62 to cycle the tape transport from the D to the H position and to store in the stop position address register 50 the reading of the bi-directional counter 44 corresponding to the position D.

When the position H is reached, the sequence control circuit 48 sends a signal to the timing circuit 64 via conductor 66 to indicate the end of the tape movement cycle.

In the preferred embodiment, the tape movement cycle will be repeated in a number of seconds selected by the operator by means of a series 68 of switches on the control panel 40. One of the switches 68 produces an infinite time delay between cycles so that manual control is required in place of the automatic cycling feature.

The control panel further includes switches 70 by which the operator can select, within limits, the length of the segment played back and the direction along the tape in which successive segments progress. Another series of switches 72 on the control panel permit the operator to move the tape rapidly in the forward and reverse directions and to stop the tape. One of the switches 72 permits the tape to be advanced at a speed suitable for scanning the tape initially to determine which portions of it are of interest. In the preferred embodiment, either 8 or 16 seconds of data can be stored in the memory for presentation on the display 32. Because the capacity of the memory 30 is finite, greater resolution can be obtained if only 8 seconds of data are stored at any one time.

Because the signal from the playback head is an analog signal in the preferred embodiment, the analog-to-digital converter 74 is provided to convert the signal to digital form for storage in the random access memory 30. The signal recalled from the memory 30 is converted to analog form for display by the digital-to-analog converter 76. In the preferred embodiment, the display 32 includes a cathode ray tube on which a representation of the played back signal is produced and the graphic recorder 34 is a strip chart recorder which produces a chart of the signal as a function of time. In other embodiments, the graphic recorder could include provision for printing selected portions of the played back signal in numerical, symbolic, or alpha-numeric form.

Thus, there has been described a system for playing back signals stored in a magnetic tape, in which the signals are always played back at a higher speed than that at which they were recorded and with the magnetic tape always moving in the forward direction during playback. The reproduced signals are stored pending display and are displayed at a lower speed for detailed analysis. This is accomplished in the present invention by intermittently playing back selected segments of the magnetic tape at high speed. The segments selected may overlap if desired or may adjoin one another end-to-end. The memory used for storing the reproduced signals pending display is of relatively limited capacity and hence is relatively inexpensive.

Although the foregoing detailed description is illustrative of the preferred embodiment of the invention, it is to be understood that additional embodiments will be obvious to those skilled in the art. The embodiments described herein together with those additional embodiments are considered to be within the scope of the invention.

What is claimed is:

1. Apparatus including a playback head for playing back signals recorded on a magnetic tape, comprising in combination:

tape transport means alternately moving the magnetic tape in opposite directions with respect to the playback head, said tape transport means moving the magnetic tape only once in each of said opposite directions to complete each tape movement cycle;

tachometer means operatively associated with said tape transport means for generating an enabling signal when a first predetermined point on the magnetic tape is located for sensing by the playback head;

gate means connected to the playback head and to said tachometer means and responsive to the enabling signal to selectively pass the signal sensed by the playback head; and, storage means connected to said gate means for storing the signal selectively passed by said gate means as said tape transport means moves the tape in a first direction from said first predetermined point on the magnetic tape to a second point on the magnetic tape, said first predetermined point and said second point being determined by said tachometer means for each successive tape movement cycle.

2. The apparatus of claim 1 wherein said tape transport means moves the magnetic tape further in a first direction than in the opposite second direction to produce a progressive interrupted playing back of signals recorded on successive segments of the magnetic tape.

3. The apparatus of claim 1 wherein said tachometer means is responsive to the direction of motion of the magnetic tape and generates the enabling signal only when the magnetic tape is moving in a predetermined one of the opposite directions.

4. The apparatus of claim 1 wherein said tape transport means moves the magnetic tape at a substantially constant speed when said gate means is selectively passing the signal sensed by the playback head.

5. The apparatus of claim 4 wherein said substantially constant speed is a different speed from the speed at which the tape was moving when the signals were recorded on it.

6. The apparatus of claim 1 wherein said tachometer means predetermines said second point on the magnetic tape as being located a preselected distance along the magnetic tape from said first preselected point.

7. The apparatus of claim 1 wherein said first predetermined point of each successive tape movement cycle is determined by said tachometer means to be between said first predetermined point and said second point of the immediately preceding tape movement cycle, whereby successive overlapping segments of the magnetic tape are played back in a progressive interrupted sequence.

8. The apparatus of claim 1 wherein said first predetermined point of said successive tape movement cycle, is determined by said tachometer means to be identical to said second point of the immediately preceding tape movement cycle, whereby successive contiguous segments of the magnetic tape are played back in a progressive interrupted sequence.

9. The apparatus of claim 1 wherein said storage means further comprises digital memory means.

10. The apparatus of claim 9 wherein the signals recorded on the magnetic tape are in digital form.

11. The apparatus of claim 9 wherein the signals recorded on the magnetic tape are in analog form, and further comprising an analog-to-digital converter connected in the path of the signal sensed by the playback head for converting that signal to a digital form.

12. The apparatus of claim 1, further comprising display means connected to said storage means for selectively displaying the signal stored by said storage means.

13. The apparatus of claim 12 wherein said display means further comprises a cathode ray tube.

14. The apparatus of claim 1, further comprising graphic means connected to said storage for selectively producing a substantially permanent graphic representation of the signal stored by said storage means.

15. The apparatus of claim 14 wherein said graphic means further comprises a strip chart recorder.

16. The apparatus of claim 14 wherein said graphic means further comprises a numerical printer.

17. A method for producing real time representation of a signal recorded over a given time interval on a continuous segment of a magnetic tape, comprising the steps of:
   playing back the segment of the magnetic tape at a speed faster than that at which it was recorded to obtain a high speed reproduction of the signal by moving the magnetic tape a first predetermined distance in a first direction then moving the magnetic tape a second predetermined distance in a second direction opposite the first direction, the entire segment being played back during the motion in the first direction; and,
   displaying the high speed reproduction of the signal during a time interval equal to the time interval that was used in recording the signal on the magnetic tape.

18. The method of claim 17 further comprising the intermediate step of:
   storing the high speed reproduction of the signal for use in generating a display thereof.

19. The method of claim 18 further comprising the additional steps of:
   repeating the playing and storing steps for selected segments of the magnetic tape, prior to repeating the displaying step for each of the selected segments.

20. The method of claim 19 wherein the repeating step further comprises selecting on each repetition a segment which partially overlaps the immediately preceding segment.

21. The method of claim 19 wherein the repeating step further comprises selecting on each repetition a segment which adjoins the immediately preceding segment.

22. The method of claim 17 wherein said first distance in the first direction is greater than said second distance in the second direction, whereby the magnetic tape progresses in the first direction by an alternating motion.

23. The method of claim 1 wherein said first distance in the first direction is less than said second distance in the second direction whereby the magnetic tape progresses in the second direction by an alternating motion.

24. A method for producing a real time representation of a signal recorded on a continuous segment of a magnetic tape moving at a so-called real time speed, and played back by using a tape transport to move the magnetic tape past a playback head at a speed faster than the real time speed, said method comprising:
   moving the magnetic tape cyclically in opposite directions with respect to the playback head in such a manner that successive cycles of movement include the movement of successive contiguous segments of the tape in the same one direction past the playback head, the speed of movement during playback being greater than the real time speed;
   storing the successive segments of the signal sensed by the playback head during the time the successive segments of the tape are passing the playback head in said one direction; and,
   displaying each of the stored successive segments of the signal for a time interval equal to the time interval that was used in recording the segment of the signal on the magnetic tape.

* * * * *